United States Patent [19]

Tehrani

[11] Patent Number: 4,909,259
[45] Date of Patent: Mar. 20, 1990

[54] METHOD AND APPARATUS FOR DETERMINING METABOLIC RATE RATIO

[76] Inventor: Fleur T. Tehrani, 2450 E. Nutwood, Apt. E 15, Fullerton, Calif. 92631

[21] Appl. No.: 341,413

[22] Filed: Apr. 21, 1989

[51] Int. Cl.$^4$ ............................................. A61B 5/08
[52] U.S. Cl. ..................................... 128/718; 128/670
[58] Field of Search ............... 128/718, 719, 670, 671, 128/696, 713, 687

[56] References Cited

U.S. PATENT DOCUMENTS

| | | | |
|---|---|---|---|
| 3,802,698 | 4/1974 | Burian et al. | 272/57 |
| 3,870,034 | 3/1975 | James | 128/2.1 |
| 3,874,233 | 4/1975 | Sanctuary et al. | 73/194 |
| 3,910,260 | 10/1975 | Sarnoff et al. | 128/2.06 |
| 4,034,745 | 7/1977 | Bloom | 128/2.06 |
| 4,038,976 | 8/1977 | Hardy et al. | 128/285 |
| 4,058,118 | 11/1977 | Stupay et al. | 128/2.06 |
| 4,181,134 | 1/1980 | Mason et al. | 128/689 |
| 4,197,857 | 4/1980 | Osborn | 128/718 |
| 4,211,239 | 7/1980 | Raemer et al. | 128/716 |
| 4,221,224 | 9/1980 | Clark | 128/718 |
| 4,239,048 | 12/1980 | Steuer | 128/666 |
| 4,368,740 | 1/1983 | Binder | 128/718 |
| 4,572,208 | 2/1986 | Cutler et al. | 128/718 |
| 4,753,245 | 6/1988 | Gedeon | 128/718 |

OTHER PUBLICATIONS

W. Fincham and F. T. Tehrani, "On The Regulation of Cardiac Output and Cerebral Blood Flow", *J. Biomed, Eng.*, vol. 5, pp. 73–75, Jan., 1983.

Primary Examiner—Lee S. Cohen
Assistant Examiner—Scott Getzow
Attorney, Agent, or Firm—Woodcock Washburn Kurtz Mackiewicz & Norris

[57] ABSTRACT

An apparatus and method determines the metabolic rate ratio (MRR) of a patient from data indicative of (a) oxygen and carbon dioxide concentrations of the patient, and (b) a cardiac function of the patient. The cardiac function data may be either heart rate and stroke volume of the patient, or cardiac output data from a cardiac output monitor than noninvasively and continuously monitors cardiac output. A $CO_2$ analyzer and either an $O_2$ analyzer or a pulse oximeter may be employed to provide the oxygen and carbon dioxide concentration data. Heart rate data is provided by either a pulse monitor or is obtained from the patient's ECG. The present invention permits measurement of MRR at any level of patient activity as well as during transitions in activity.

31 Claims, 10 Drawing Sheets

METHOD AND APPARATUS FOR DETERMINING METABOLIC RATE RATIO

FIELD OF THE INVENTION

The present invention relates to a method and apparatus for determining a patient's metabolic rate ratio. More particularly, the present invention relates to a method and apparatus for determining a patient's metabolic rate ratio from (1) data indicative of carbon dioxide and oxygen pressures of the patient's arterial blood and (2) data indicative of either (a) the patient's heart rate and stroke volume, or (b) the patient's cardiac output if monitored noninvasively and continuously.

BACKGROUND OF THE INVENTION

Devices for determining the metabolic rate of a patient are generally known in the art. Known devices measure the patient's oxygen uptake by one means or another to provide a measure of metabolic rate. For example, U.S. Pat. No. 4,572,208, discloses a method and apparatus that measures oxygen uptake as an indicator of metabolic rate. Oxygen uptake can be measured: on a breath-by-breath basis, as taught by U.S. Pat. No. 4,368,740; by introducing a known amount of an inert gas (i.e., helium) into the patient's airways, as taught by U.S. Pat. No. 4,221,224; or by using an airtight system for patients under artificial respiration, as taught by U.S. Pat. No. 4,753,245.

These and other techniques require a system (either closed or open) for measuring the patient's oxygen consumption. In a closed system, a container of gas is required through which the patient inhales and exhales. Closed systems are acceptable for measurements taken under steady state conditions only. In an open system, the patient's amount of inhaled and exhaled gas are carefully monitored. In some systems, oxygen uptake is measured on a breath-by-breath basis. These systems require sophisticated sensors and gas flow meters to provide continuous output data during short transition periods.

In addition to the drawbacks noted above, a problem with using oxygen uptake as an indicator of metabolic rate is that the oxygen uptake of the human body reflects the rate of metabolism under steady state conditions only. Therefore, during transition periods in exercise and recovery, the patient's oxygen uptake cannot be used as a reliable indicator of metabolic rate.

The present invention is based upon the inventor's finding that a patient's metabolic rate ratio (MRR) can be reliably determined under both steady state and transient conditions without measuring oxygen uptake by employing data indicative of the patient's carbon dioxide and oxygen pressures of arterial blood and the patient's cardiac output. MRR is the ratio of the metabolic rate to basal rate of metabolism. In the practice of the invention, cardiac output data may be obtained by measuring heart rate and stroke volume. Various techniques have been described in the prior art for measuring heart rate. U.S. Pat. Nos. 4,034,745, 4,181,134, and 4,239,048 are representative. However, the prior art does not employ heart rate data to determine MRR, nor does the prior art provide data indicative of heart rate as well as MRR at different levels of activity.

It is, therefore, desirable to provide a method and apparatus for determining a patient's MRR at all levels of activity without complex or cumbersome equipment and without invasive physiological measurements.

SUMMARY OF THE INVENTION

The present invention relates to a method and apparatus for determining a patient's MRR using data indicative of $CO_2$ (carbon dioxide) and $O_2$ (oxygen) pressures of the patient's arterial blood and of the patient's cardiac output. The invention is based upon the findings that cardiac output increases rapidly and enormously as the MRR increases, and cardiac output increases as arterial $CO_2$ pressure increases and as arterial $O_2$ pressure decreases.

According to the invention, data indicative of the patient's arterial blood $CO_2$ pressure may be provided by a $CO_2$ analyzer. Data indicative of the patient's arterial blood $O_2$ pressure may be provided by either an $O_2$ analyzer or by a pulse oximeter that monitors the hemoglobin oxygen saturation of arterial blood. Cardiac output data may be obtained by at least one of two methods.

In a first method, data indicative of the patient's heart rate and stroke volume is provided, and the patient's cardiac output is computed therefrom. Heart rate is measured on a continuous basis, either from the output of a pulse monitor that provides a systolic pulse signal or from an ECG (electrocardiogram) signal. The invention is not limited to these means of measuring heart rate. Stroke volume is measured either on a continuous basis or is measured once, prior to operation of the system described herein, and provided as a constant. Known means for measuring stroke volume are disclosed herein.

In a second method, data indicative of the patient's cardiac output is directly provided by a cardiac output monitor provided that such device noninvasively and continuously monitors cardiac output.

A method for measuring a patient's MRR according to the present invention comprises the steps of:

(a) providing data indicative of oxygen and carbon dioxide concentrations of the patient;

(b) determining, based upon the data indicative of the patient's oxygen and carbon dioxide concentrations and data indicative of barometric pressure, the partial pressures of oxygen and carbon dioxide in arterial blood of the patient;

(c) determining, based upon the results of step (b), net effects of oxygen and carbon dioxide in the arterial blood on cardiac output of the patient;

(d) determining, based upon data indicative of cardiac output of the patient and the result of step (c), net effect of metabolic rate ratio on blood flow of the patient; and, (e) determining, based upon the result of step (d), the metabolic rate ratio of the patient and providing output data indicative thereof.

Knowing the basal rate of metabolism, the metabolic rate can be easily obtained from the output data indicative of the metabolic rate ratio.

The data indicative of the oxygen and carbon dioxide concentrations and the data indicative of the patient's cardiac output may be obtained as described above.

Apparatus for carrying out the method of the invention may comprise:

(a) first means for providing data indicative of oxygen and carbon dioxide concentrations of the patient;

(b) second means for providing data indicative of a cardiac function of the patient;

(c) third means for processing the data provided by the first and second means and providing output indicative of the MRR of the patient by:
   (i) determining, based upon the data indicative of the patient's oxygen and carbon dioxide concentrations, and data indicative of barometric pressure, the partial pressures of oxygen and carbon dioxide in arterial blood of the patient;
   (ii) determining, based upon the results of step (i), net effects of oxygen and carbon dioxide in the arterial blood on cardiac output of the patient;
   (iii) determining, based upon data indicative of cardiac output of the patient and the result of step (ii), net effect of metabolic rate ratio on blood flow of the patient; and,
   (iv) determining, based upon the result of step (iii), the metabolic rate ratio of the patient.

According to the invention, a suitably programmed microprocessor comprises the third means and performs each of the functions thereof according to an algorithm disclosed herein. Analog to digital converters are employed to convert analog data from the $CO_2$ and $O_2$ analyzers (and/or pulse oximeter) and, if desired to be monitored continuously, stroke volume monitor to digital data for processing by the microprocessor. Heart rate data may be provided by direct digital input to the microprocessor (e.g., from a counter circuit receiving clock pulses from a pulse detector). A digital display circuit may provide a visual display of MRR and heart rate data. A digital-to-analog converter and appropriate amplification may be provided to drive additional circuitry, for example, a chart recorder, as desired.

It is an object of the present invention to provide an apparatus and method for reliably measuring a patient's metabolic rate ratio during periods of activity, rest and transition therebetween of a patient.

It is a further object of the present invention to provide a system for determining a patient's metabolic rate ratio using data indicative of $CO_2$ and $O_2$ pressures of the patient's arterial blood and cardiac output, the latter either being computed from heart rate and stroke volume data provided to the system or being provided by a cardiac output monitor, if of a type that noninvasively and continuously monitors cardiac output. In the inventor's presently pending patent application, Ser. No. 233,455, mention is made of using a metabolic rate ratio monitor to provide additional data to the controller of an artificial respirator. The apparatus and method described herein may be used to provide the required data to the system disclosed in that application. The output data provided by the apparatus of the present invention can also be used in exercise monitoring systems and many other similar applications.

These and other novel objects, advantages and features of the present invention will become more apparent from the following detailed description and appended claims.

DETAILED DESCRIPTION OF THE PREFERRED EMBODIMENT

The invention is described herein in four sections as follows: introduction to apparatus of the invention; apparatus according to the invention; introduction to method of the invention; and, method according to the invention.

Introduction to Apparatus

The present invention employs data indicative of the $CO_2$ and $O_2$ pressures of a patient's arterial blood and of the patient's cardiac output to calculate the patient's metabolic rate ratio. Cardiac output data may be obtained by at least one of two methods.

In a first method, data indicative of the patient's heart rate and stroke volume is provided and the patient's cardiac output is computed therefrom. Heart rate data is obtained from a systolic pulse signal provided by a pulse monitor or is derived from an ECG (electrocardiogram) signal. The invention is not limited to these means of measuring heart rate. Stroke volume is provided by a noninvasive monitor of any suitable type such as described in the following U.S. patent literature and incorporated herein by reference: U.S. Pat. Nos. 4,450,527; 4,137,910; and, 4,509,526. The patient's stroke volume may be measured when the patient is in a desired posture, for example, standing, sitting or supine, using any of the techniques disclosed in the above patents, or many other techniques known to those skilled in the art, prior to operation and provided to the system as a constant.

In a second method, data indicative of the patient's cardiac output is directly provided by a cardiac output monitor provided that such device noninvasively and continuously monitors cardiac output. Such apparatus have been described in the patent literature. See, e.g., U.S. Pat. Nos. 4,437,469 and 4,676,253, incorporated herein by reference.

$CO_2$ and $O_2$ analyzers coupled to receive exhaled gas from a patient may be employed to provide the data indicative of the arterial pressures of $CO_2$ and $O_2$. Alternatively, in the case of $O_2$, a pulse oximeter may be employed to provide the same data by monitoring the hemoglobin $O_2$ saturation of arterial blood.

According to the disclosed embodiment, the apparatus includes a microprocessor for processing this data and determining therefrom the patient's MRR according to the method described herein.

Apparatus

Figure 1:
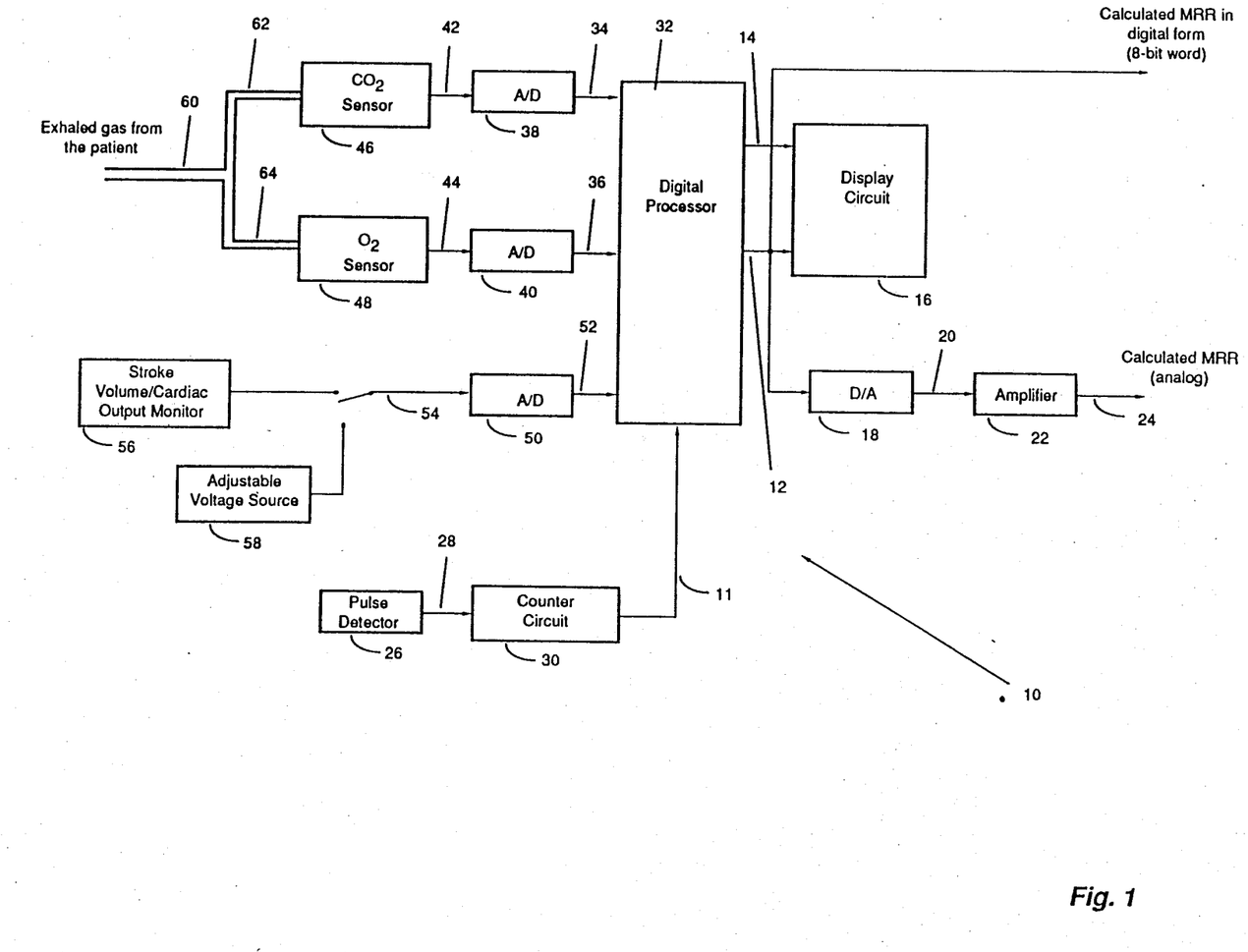
FIG. 1 is a block diagram of an MRR measuring system embodying the present invention.

Referring now to the drawings wherein the like reference numbers represent like elements, there is illustrated in FIG. 1, in summary detail, a preferred embodiment of a measuring/monitoring system provided in accordance with this invention and designated generally as 10. As shown, exhaled gas from a patient is passed through an expiration line 60. Expiration line 60 is coupled at one end to $CO_2$ and $O_2$ sensors 46, 48 via inlets 62, 64. The other end is coupled to an endotracheal tube or a mouthpiece (not shown) which is used to collect the patient's exhaled gas. The exhaled gases from the patient are analyzed by the $CO_2$ and $O_2$ sensors 46, 48 to provide data indicative of the patient's concentrations of $CO_2$ and $O_2$, respectively. (If system 10 is employed as an exercise monitoring system for a normal healthy subject, analysis of the exhaled gases will not be necessary since the arterial pressures of $O_2$ and $CO_2$ for the subject in light to moderate exercise do not differ significantly from their normal values at rest.)

In an alternative embodiment, the $O_2$ sensor 48 may be substituted with a pulse oximeter in which case the exhaled gases will pass to $CO_2$ sensor 46 only. The output of a pulse oximeter represents the hemoglobin $O_2$ saturation of the arterial blood and can be converted to the arterial pressure of $O_2$. Reference will hereafter be made to $O_2$ analyzer 48, but it should be understood that, except as indicated, this is not intended to exclude substitution of a pulse oximeter, and therefore, all such references include a pulse oximeter.

Analog signals 42 and 44 from the two sensors 46, 48 are converted to digital data by two A/D converters 38 and 40. This digital data is provided to a processor 32 as shown at 34, 36. The processor may be a Micromint brand BCC52 Basic controller board, however, any suitable processor may be employed. The A/Ds 38, 40 may comprise a portion of a multiple channel A/D board that samples the input signals and converts them to digital outputs at a fixed rate, e.g., every 640 microseconds. Outputs 34 and 36 may be two output channels of the A/D board.

The patient's stroke volume may comprise another input to processor 32. If provided, the stroke volume can either be continuously monitored using an appropriate noninvasive measuring technique or measured prior to operation of the system at any desired posture and applied as a constant input to the system. The latter is possible since stroke volume is affected mainly by the subject's posture and, after a slight increase during the transition from rest to exercise, remains fairly constant at different levels of activity. Stroke volume may be measured by a monitor 56 of a type described above and an analog output 54 therefrom, representing the patient's stroke volume, may be applied to the input of an A/D converter 50. Alternatively, if it is not desired to monitor stroke volume continuously, a representative value (e.g., obtained from the patient prior to operation of the system) may be stored in software of the processor 32 or supplied to the input of A/D converter 50 from a fixed adjustable voltage source 58. The digital output of the A/D 52 is supplied to the digital processor 32 as shown.

A pulse detector 26 may provide a systolic pulse signal 28 to counter circuit 30. A pulse detector with a photoelectric cell transducer may be used to detect systolic pulses of the subject, for example, at the finger. Alternatively, the patient's ECG signal can be provided as the input to counter 30. The counter 30, whose output represents the patient's heart rate, counts the number of signals occurring over a selected period of time, e.g., every 15 seconds, and provides this count to processor 32 as shown at 11.

The processor 32 is shown as providing two digital outputs. One of the outputs 12 provides the calculated digital value of the patient's MRR. The other output 14 provides the patient's heart rate in beats per minute. The first output 12 is coupled to a D/A converter 18. The output 20 of D/A converter 18 is applied to an amplifier circuit 22. The output of the amplifier 24 is an analog signal indication of the patient's metabolic rate ratio and may be used to drive additional circuitry such as a chart recorder. In preferred embodiments, output 24 varies from 0.6 to 4.2 volts for MRRs between 1 and 7. As shown, the processor's outputs 12 and 14 are applied to a display circuit 16 for providing a visual display of the output data.

Figure 2:
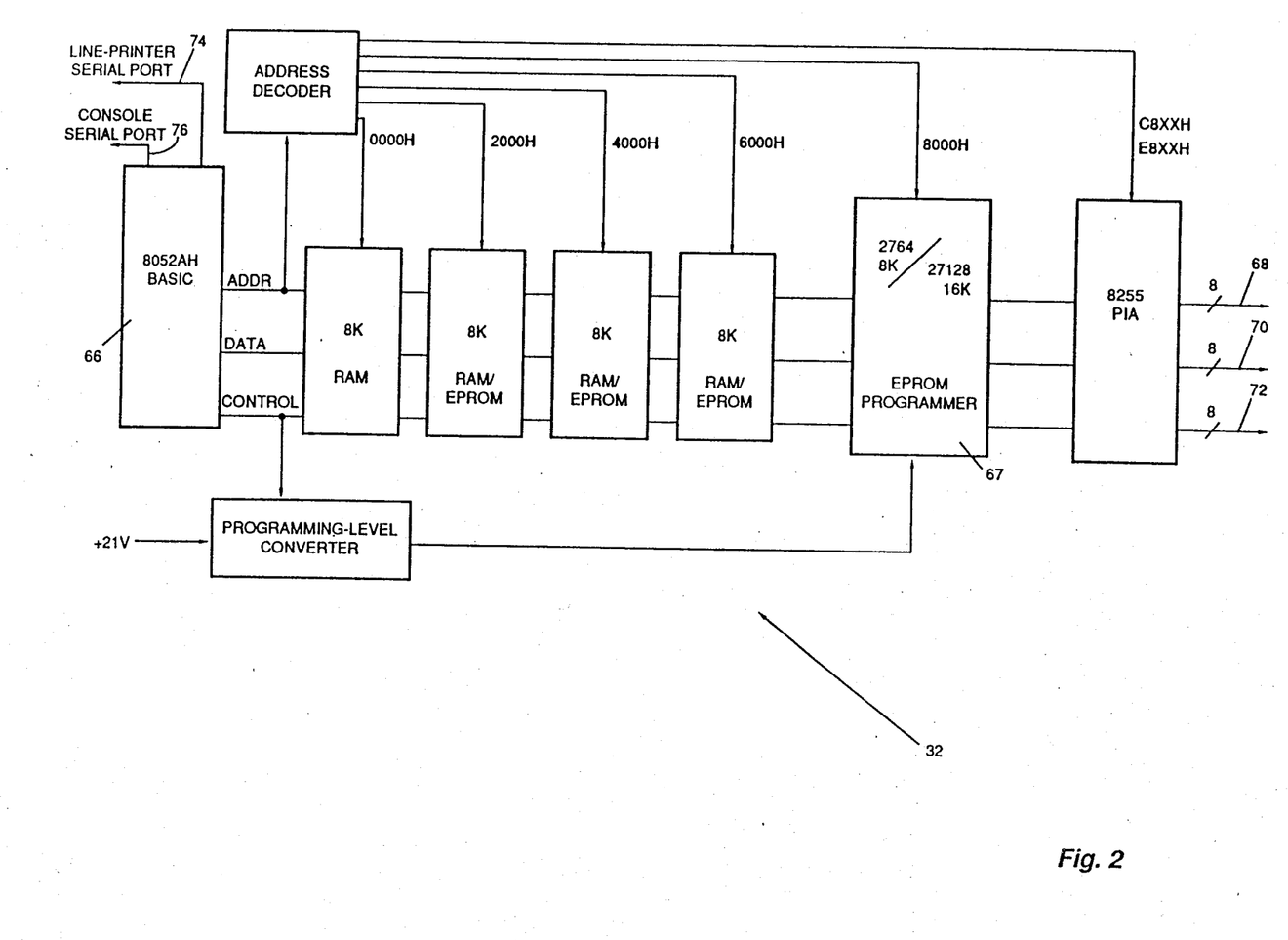
FIG. 2 is a block diagram of a programmable processor employed in a preferred embodiment of the present invention.

In the schematic diagram of FIG. 2, a block diagram of processor 32 is illustrated. Processor 32 may employ an Intel 8052AH-BASIC, 8-bit microcontroller chip 66 which contains 8k bytes ROM on the chip as a BASIC interpreter and 256 bytes of RAM. The processor 32 has 48K bytes of RAM/EPROM, a 2764/128 EPROM programmer, three parallel I/O ports designated as 68, 70 and 72, a serial line printer port 74, and a serial terminal port 76. 8052AH-BASIC chip 66 has a 16-bit address and an 8-bit data bus. The eight least significant address bits and the data bus are multiplexed together. Preferably, the control program is saved on an EPROM and is executed continuously after resetting the processor at the beginning of operation.

Figure 4:
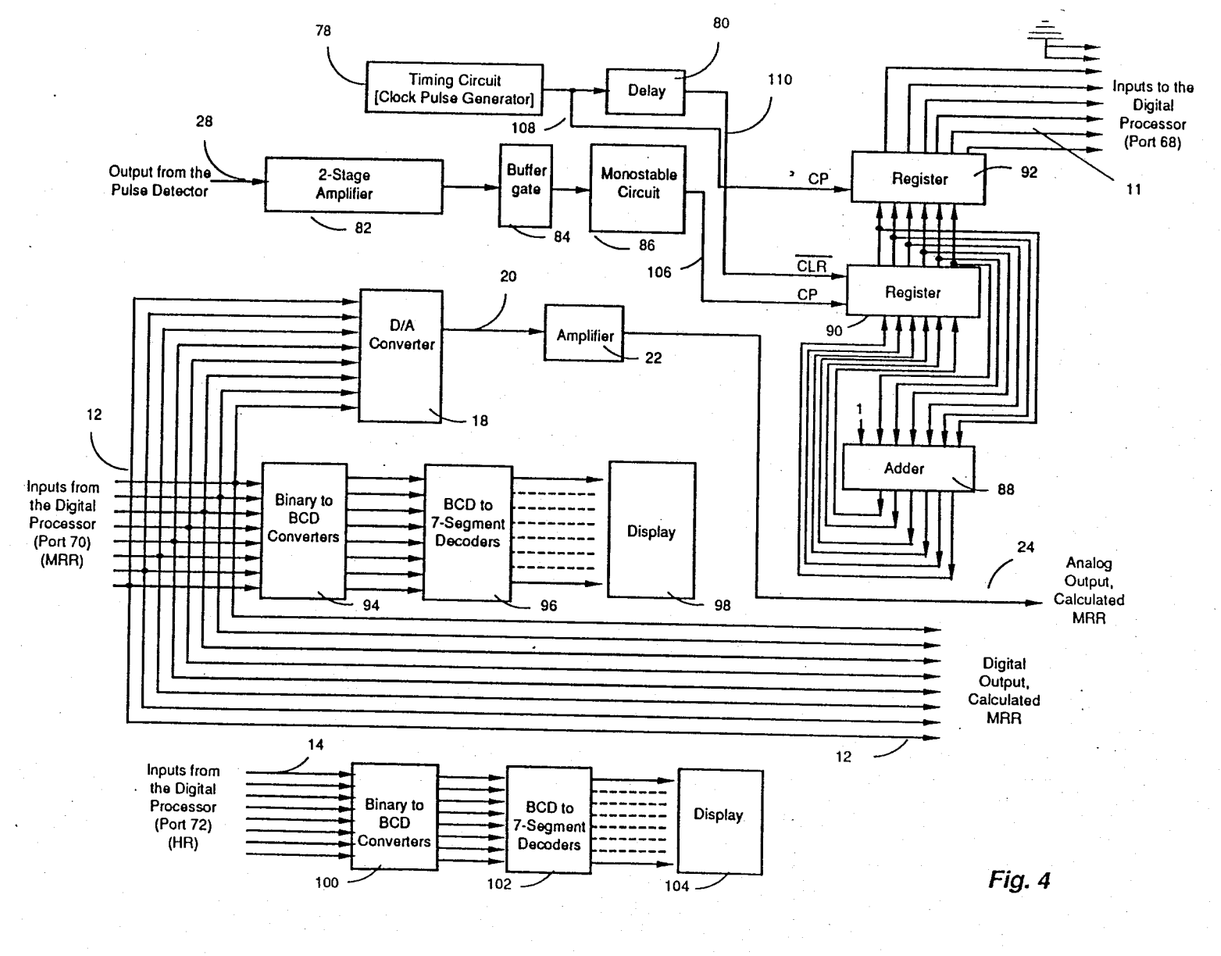
FIG. 4 is a detailed block diagram of a preferred embodiment of circuitry for practicing the present invention.

Referring to FIG. 4, counter circuit 30, display circuit 16, D/A converter 18 and amplifier 22 are illustrated in greater detail. The output from pulse detector 28 is applied to a 2-stage amplifier 82. The 2-stage amplifier is designed so that the current drawn from the pulse detector circuit is limited. The output of this amplifier is applied to a buffer gate 84 which provides either zero or five volts corresponding respectively to low and high levels of the input voltage. The sequence of pulses at the output of the buffer gate 84 is applied to a monostable circuit 86 which acts as a clock pulse generator for register circuit 90. Monostable circuit 86 acts as a pulse shaper and generates a train of sharp and clean pulses 106 for register circuit 90.

Timing circuit 78 generates a clock pulse at a specific frequency. In preferred embodiments, the period of this clock pulse is 15 seconds, but can be reduced if necessary. The output of timing circuit 78, designated at 108, is a clock pulse for register circuit 92. Output 108 is delayed by about 70 nanoseconds by delay circuit 80, and the output of the delay circuit, designated as 110, is applied to the clear line of register 90. The 6-bit output of register 90 is the input to 6-bit adder 88. The least significant bit of one of the inputs to the adder circuit 88 is permanently connected to logic "1", and the other bits are at logic "0", i.e., grounded.

The other 6-bit input is connected to the outputs of register 90. The outputs of adder 88 provide the 6-bit input to register 90. The outputs of register 90 are also connected to the inputs of register 92. When a pulse arrives on 110 at the clear line of register 90, the outputs of register 90 are cleared. Then, by arrival of every pulse at 106 (output 106 represents the heartbeat sequence), the 6-bit input of the parallel-in parallel-out register 90 appears at its output. This output is immediately incremented by "1" at the output of adder 88. The output of adder 88 is connected to the input of register 90.

Therefore, by arrival of every pulse at 106, the output of register 90 is incremented by "1" until another pulse appears at 108 after a specific period, e.g., 15 seconds. At this time, register 92 is clocked, and the output of register 90 is transferred to the output of register 92. After a delay of about 70 nanoseconds which is used to provide sufficient time for the transfer of the inputs to the outputs of register 92, the pulse generated at 108 appears at 110 and clears the register 90.

This procedure is repeated, e.g. every 15 seconds. Thus, the 6-bit output of register 92 is the number of heartbeats counted over a 15-second period. This 6-bit word is shifted 2 bits to the left, which is the same as being multiplied by a factor of 4, and the resulting 8-bit word 11 is applied to port 68 of the main processor. Output 12 from port 70 of the main processor, which is an 8-bit word representing the calculated value of the metabolic rate ratio, is accessible at the output of the circuit. This value is also converted to analog using a D/A converter 18 and amplified by an amplifier circuit 22 and is accessible at the output of the circuit to represent the calculated value of the MRR in analog form 24. In preferred embodiments, this analog voltage varies from 0.6 to 4.2 volts for MRRs changing between 1 and 7.

The digital word 12 from port 70 of the main processor is also applied to a binary to BCD converter circuit 94. The outputs of this circuit are used as the inputs to circuit 96 which are BCD to 7-segment decoders. The outputs from block 96 are applied to 7-segment LEDs, circuit 98, which displays the value of the MRR. The other output of the main processor from port 72, which is an 8-bit word representing the heart rate in beats per minute, is applied to another binary to BCD converter circuit 100. The outputs of 100 are used as the inputs to circuit 102 which are BCD to 7-segment decoders. The outputs of 102 are applied to 7-segment LEDs, circuit 104, to display the heart rate in beats per minute.

Figure 5A:
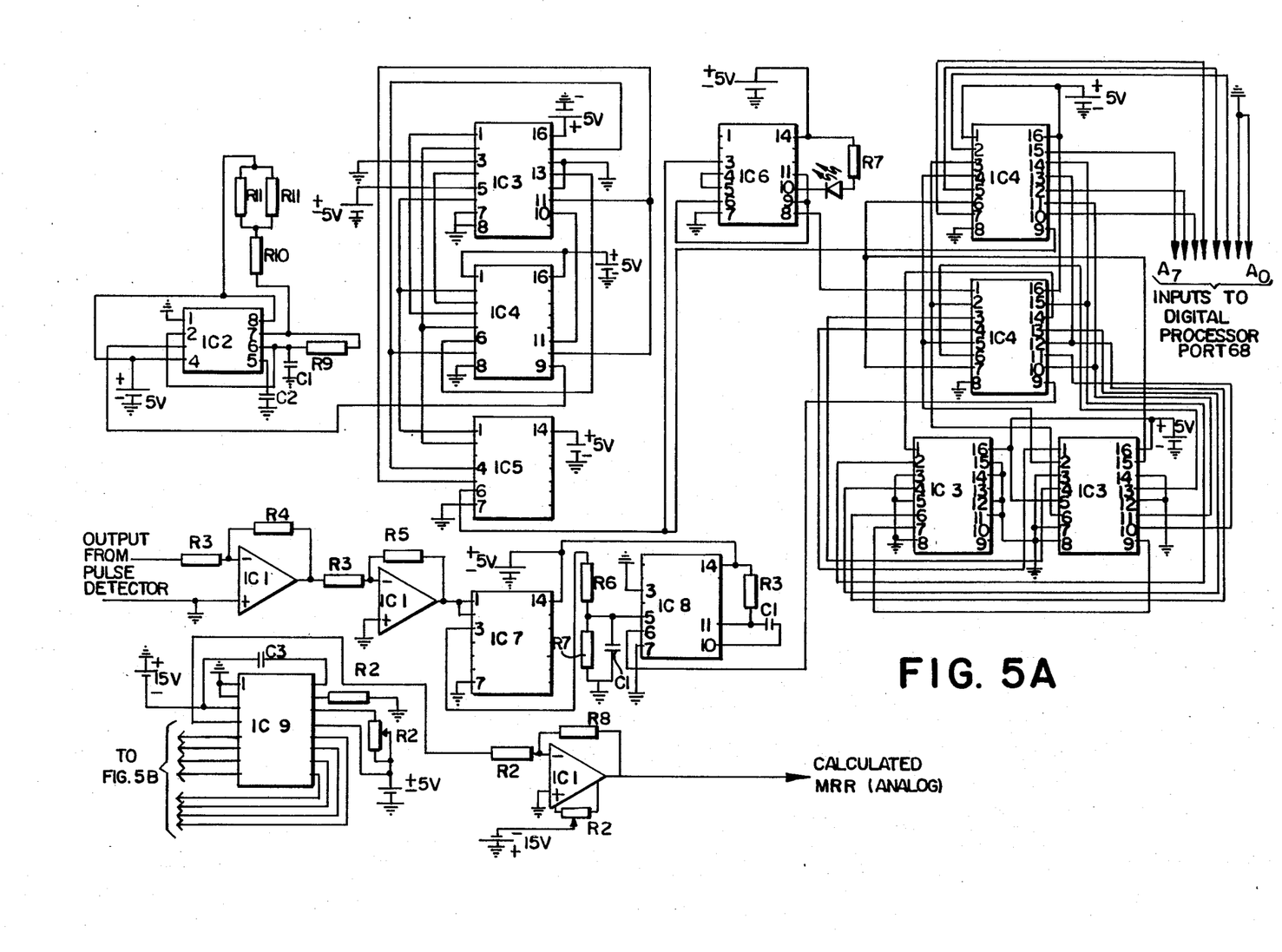
FIGS. 5A, 5B and 5C are a circuit diagram illustrating a preferred embodiment of the block diagram of FIG. 4.
Figure 5B:
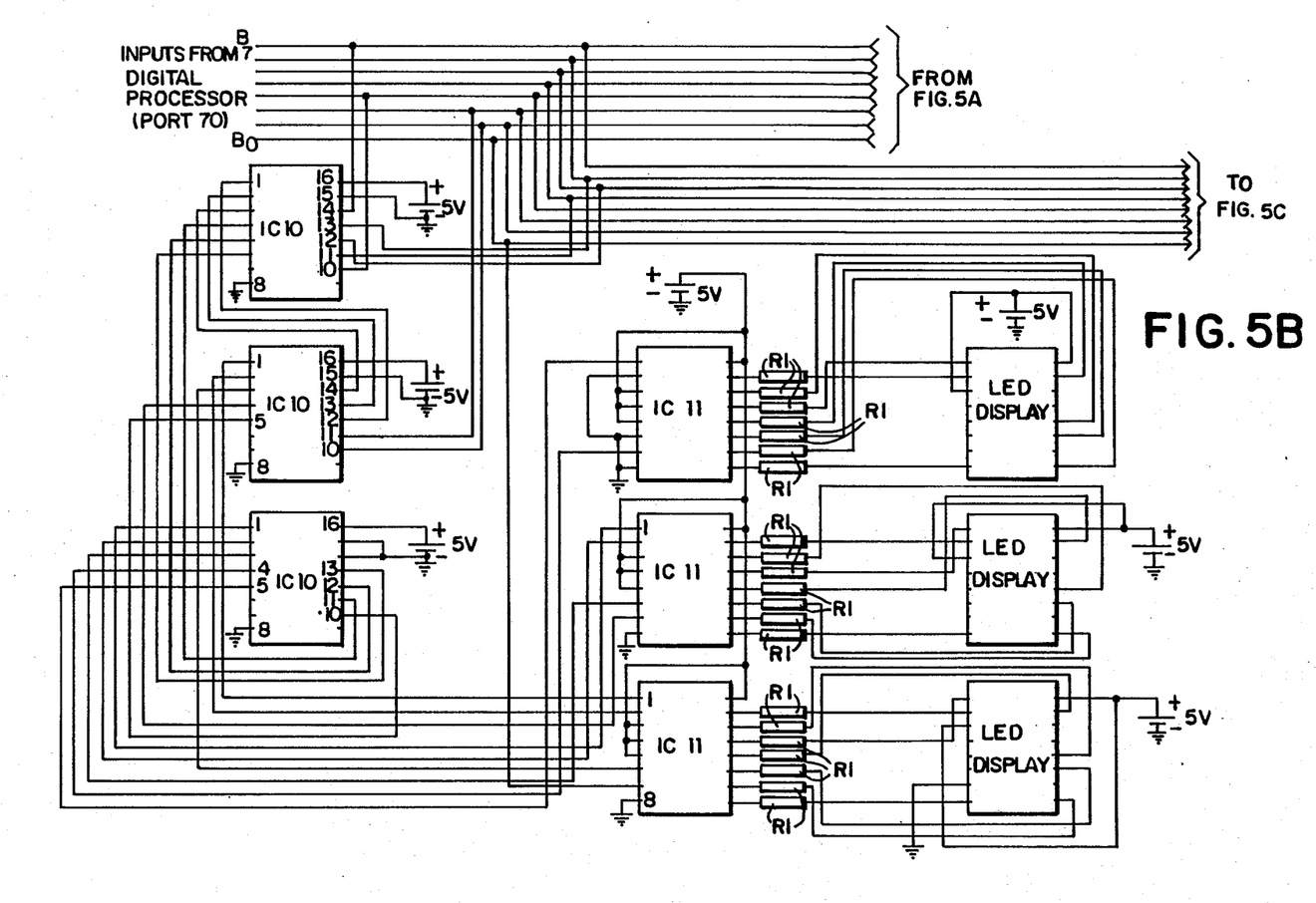
Figure 5C:
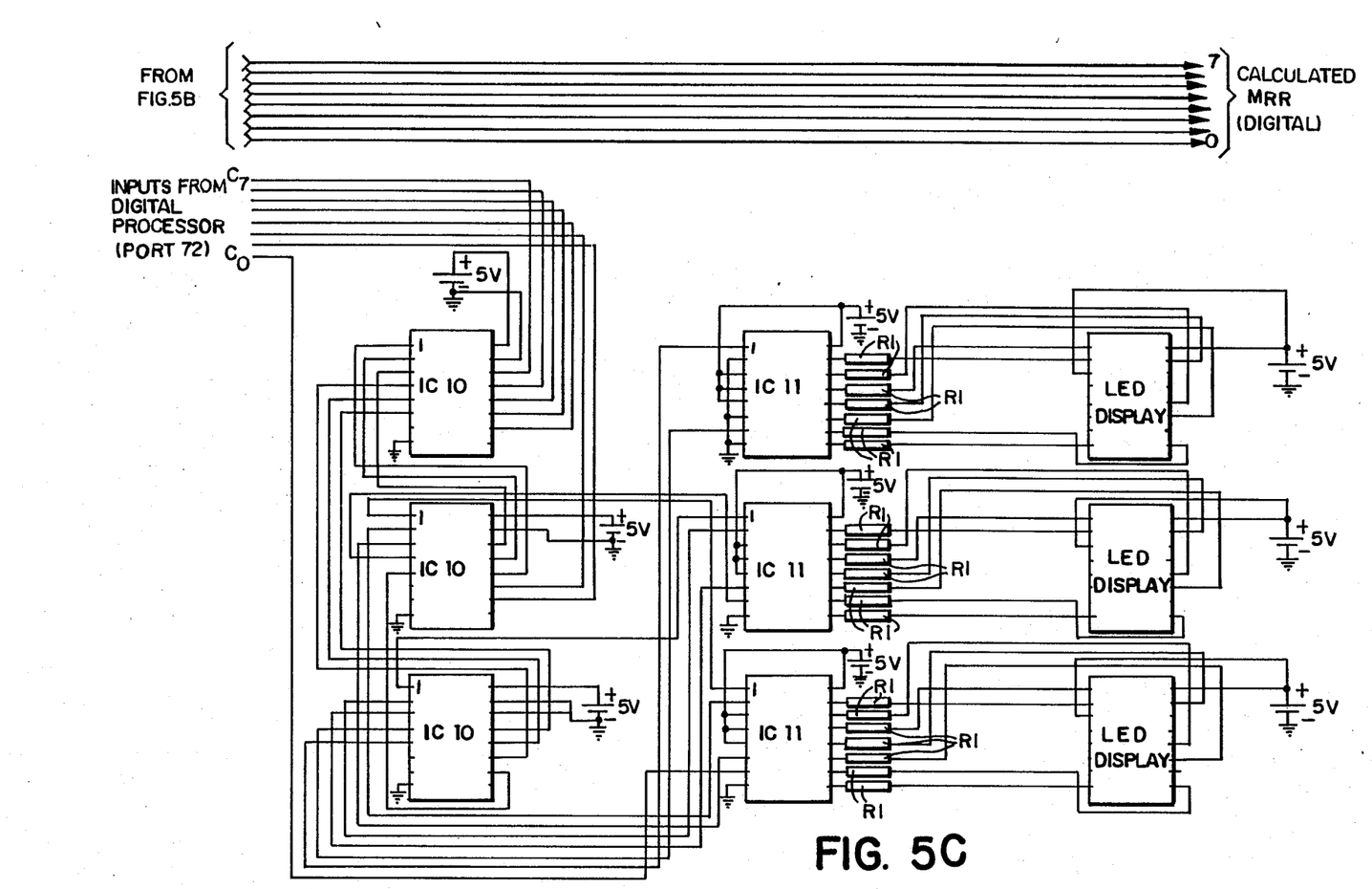

FIGS. 5A, 5B and 5C are a detailed circuit diagram illustrating counter circuit 30, D/A converter 18, amplifier circuit 22 and display circuit 16. The component types and their values are shown in the chart below.

| NAME | COMPONENT ID OR VALUE | NAME | COMPONENT ID OR VALUE |
|---|---|---|---|
| R1 | 150 ohms | IC3 | SN74LS283N |
| R2 | 1K ohms | IC4 | SN74LS174ND |
| R3 | 10K ohms | IC5 | N7421A |
| R4 | 100K ohms | IC6 | SN7404N |
| R5 | 22K ohms | IC7 | MC14071 |
| R6 | 100K ohms | IC8 | SN74121N |
| R7 | 390 ohms | IC9 | AM14088N |
| R8 | 2.7K ohms | IC10 | SN74185AN |
| R9 | 6.5 M ohms | IC11 | SN7447AN |
| R10 | 1 M ohms | | |
| R11 | 620K ohms | | |
| C1 | 0.1 micro farad | | |
| C2 | 0.01 micro farad | | |
| C3 | 11 pico farad | | |
| IC1 | 741CN | | |
| IC2 | CA555C6 | | |

Introduction to Method

Cardiac output can be considered as a function of the rate of metabolism and the $CO_2$ and $O_2$ pressures of arterial blood. The patient's blood flow can be modeled as:

$$\frac{dQ}{dT} = Q'_M + Q'_C \quad \text{(equation 1)}$$

where $dQ/dT$ is the cardiac output or the blood flow, $Q'_C$ is a function of the arterial pressures of $CO_2$ and $O_2$, and $Q'_M$ is a function of the metabolic rate. The relationship between the cardiac output and $CO_2$ pressures of arterial blood can be expressed as:

$$Q'(CO_2) = 0.0045 \,(pACO_2\text{-}42), \text{ for } PaCO_2 > 42 \text{ mm Hg} \quad \text{(equation 2)}$$

and:

$$Q'(CO_2) = 0, \text{ for } PaCO_2 \leq 42 \text{ mm Hg}. \quad \text{(equation 3)}$$

In equations 2 and 3, $Q'(CO_2)$ is the net effect of the arterial pressures of $CO_2$ on the cardiac output in liters/second and $PaCO_2$ represents the partial pressure of $CO_2$ in the arterial blood in millimeters of mercury (mm Hg).

The relationship between cardiac output and the arterial $O_2$ pressure is provided using the following mathematical expressions:

$$Q'(O_2) = 244.509 \times 10^{-4} T_0(X) - 323.328 \times 10^{-4} T_1(X) + 105.044 \times 10^{-4} T_2(X) - 143.505 \times 10^{-5} T_3(X),$$

$$\text{for } PaO_2 < 95 \text{ mm Hg,}$$

and:

$$Q'(O_2) = 0, \text{ for } PaO_2 \geq 95 \text{ mm Hg} \quad \text{(equation 5)}$$

where:

$$X = \frac{2PaO_2 - 115}{65}. \quad \text{(equation 6)}$$

In the above expressions, $Q'(O_2)$ is the net effect of the arterial pressure of $O_2$ on the cardiac output in liters/seconds, $PaO_2$ is the arterial pressure of $O_{20}$ in mm Hg and $T_j(X)$ is the Chebyshev polynomial of the first kind with degree (j) and argument (X). $Q'_c$, which was defined earlier as the effect of $CO_2$ and $O_2$ pressures of arterial blood on the cardiac output, can be written as:

$$Q'_c = Q'(CO_2) + Q'(O_2). \quad \text{(equation 7)}$$

$Q'_M$, defined as the net effect that the metabolic rate ratio has on the cardiac output, can be expressed as a function of the metabolic rate ratio in the following manner:

$$Q'_M = 158.5674 \times 10^{-3} T_0(Y) + 617.519 \times 10^{-4} T_1(Y) \quad \text{(equation 8)}$$

where:

$$Y = \frac{2MRR - 7}{5}. \quad \text{(equation 9)}$$

In equations 8 and 9, $Q'_M$ is expressed in liters/second, MRR represents the metabolic rate ratio and $T_j(Y)$ is the Chebyshev polynomial of the first kind of degree (j) with argument (Y). When determining the metabolic rate ratio, arterial pressures of $CO_2$ and $O_2$ are derived from the values of the input data provided by $CO_2$ and $O_2$ sensors and $Q'(CO_2)$ and $Q'(O_2)$ are calculated using equations 2, 3, 4, 5 and 6. The cardiac output can be determined from the heart rate and data indicative of the stroke volume. Then, using equations 7 and 1, $Q'_c$ and $Q'_M$ can be calculated. Alternatively, stroke volume may be measured prior to operation of the apparatus and provided as an input to the system instead of being continuously monitored, as described above. If a cardiac output monitor of the type hereinabove described is employed, then cardiac output can be taken directly from the monitor, in which case there is no need to measure heart rate or stroke volume. The metabolic rate ratio can be calculated from $Q'_m$ using equations 8 and 9. Knowing the basal rate of metabolism, the metabolic rate can be easily obtained from the output data indicative of the MRR.

The apparatus and method disclosed herein may be simplified if used for normal, healthy individuals. For a healthy subject, the arterial pressures of $CO_2$ and $O_2$ in light-to-moderate exercise remain within a normal range at rest. Under these conditions, $Q'(CO_2)$ and $Q'(O_2)$ from equations 3 and 5 will be zero, and there is no need to use $CO_2$ and $O_2$ sensors in the system.

METHOD

Referring to FIGS. 3A–3D, a flow chart of a computer program embodying the method of the present invention is illustrated.

Figure 3:
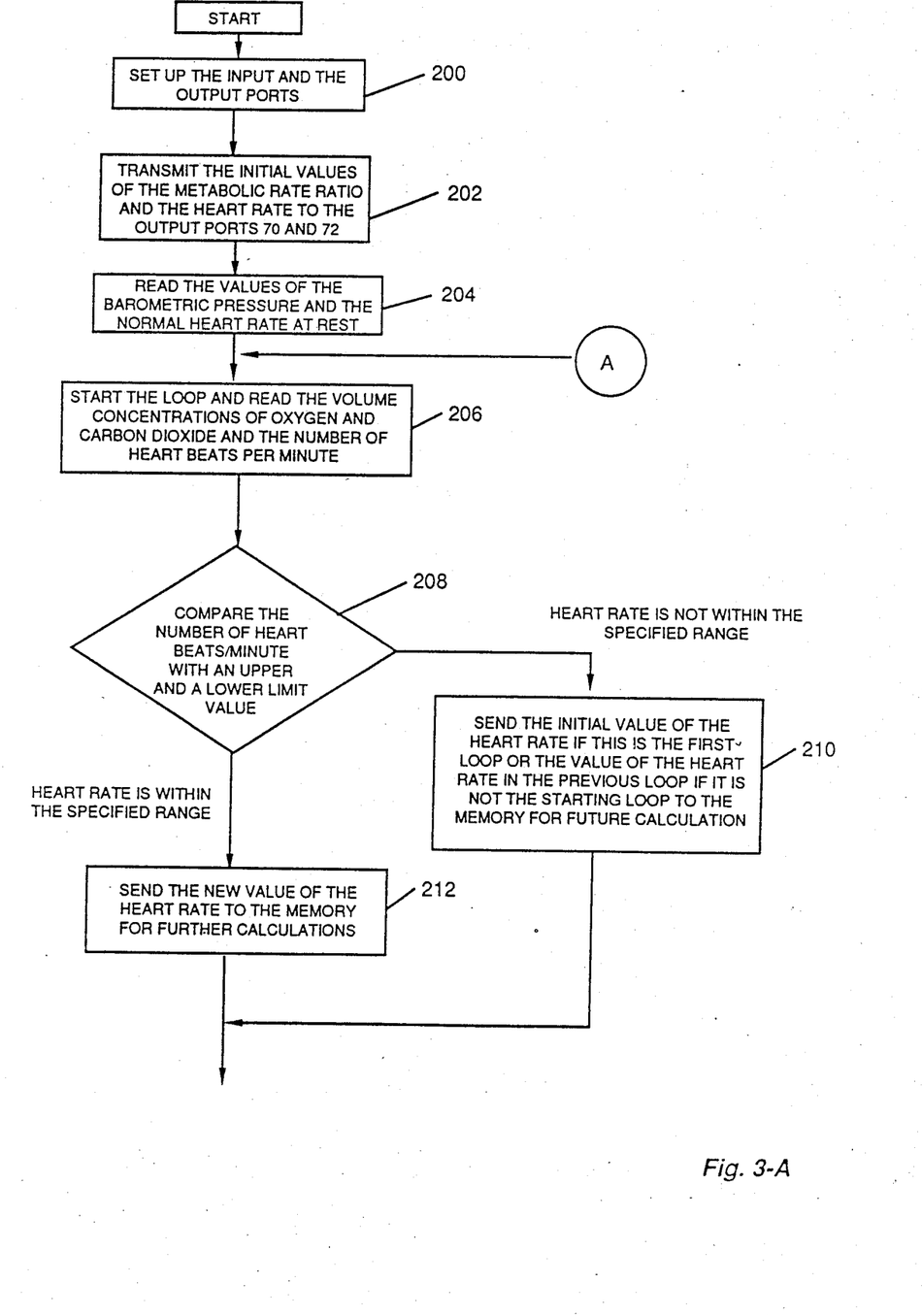
FIGS. 3A-3D are a flow chart illustrating a method for determining MRR according to a preferred embodiment of the present invention.

As can be seen at the beginning of the flow chart, the input and output ports of processor 32 are set up at 200. At the next step 202, initial values of the MRR and the heart rate at rest are transmitted to the output ports 70 and 72 of the processor 32. In step 204, values of the barometric pressure and the heart rate at rest are entered into the processor 32. These values may be supplied via two reserved channels of the A/D board or may be stored in software. At the next step 206, a program loop is started at "A" and the volume concentrations of $CO_2$ and $O_2$ in exhaled gases are entered through the A/D converters 38, 40. Also at this step, the number of heart beats per minute or the number of heart beats counted over any other specified time period from the counter circuit 30, is entered through the port 68. As mentioned, the value of arterial hemoglobin $O_2$ saturation may be supplied to the processor by using a pulse oximeter instead of an $O_2$ gas sensor.

In step 208, the number of heart beats per minute is compared with a lower and upper limit value. The limit values are typically 50 and 220 beats per minute, respectively. If the heart rate is found to be outside the specified range, step 210 is executed in which the supplied value for the heart rate is disregarded and the heart rate value used in the previous loop is maintained in the memory for future calculations. If it happens to be the first loop of program execution, the initial value of the heart rate at rest, read at the beginning of the program at step 204, is stored in memory for further calculations. If as a result of the comparison at step 208 the heart rate is found to be within the specified range, its value is accepted at step 212 and stored in memory for further computations.

At step 214, the partial pressures of $O_2$ and $CO_2$ in the patient's arterial blood are calculated using the following equations:

$$PaCO_2 = C_{CO2}(P_B - 47) - K_1 \quad \text{(equation 10)}$$

$$PaO_2 = C_{O2}(P_B - 47) - K_2, \quad \text{(equation 11)}$$

where $PaCO_2$ and $PaO_2$ are the partial pressures of $CO_2$ and $O_2$ in the arterial blood in mm Hg, $C_{CO2}$ and $C_{O2}$ are the volume concentrations of $CO_2$ and $O_2$ in the exhaled gases, $K_1$ and $K_2$ are two constants representing the average differences between the alveolar and arterial pressures of $CO_2$ and $O_2$ in mm Hg, $P_B$ is the barometric pressure in mm Hg, and 47 is the partial pressure of water vapor in the alveoli space in mm Hg. If a pulse oximeter is used for monitoring the blood $O_2$ level instead of an $O_2$ gas sensor, the following equation is used at this step to determine the partial pressure of $O_2$ in the arterial blood:

$$PaO_2 = \frac{-\ln[1 - (SaO_2)^{\frac{1}{4}}]}{0.046}, \quad \text{(equation 12)}$$

where $PaO_2$ represents the partial pressure of $O_2$ in the arterial blood in mmHg and $SaO_2$ is the arterial hemoglobin $O_2$ saturation monitored by the oximeter.

In the next step 216, the partial pressure of $CO_2$ in the arterial blood is compared with a threshold value of 42 mm Hg. If the partial pressure of $CO_2$ is less than or equal to the threshold value, step 218 is executed in which the net effect of $CO_2$ on the cardiac output is set to zero. However, if the partial pressure of $CO_2$ in the patient's arterial blood is greater than the threshold value, the net effect of $CO_2$ on the cardiac output is calculated using equation 2 at step 220.

At step 222, the partial pressure of $O_2$ in the arterial blood, $PaO_2$ is compared with a threshold value of 95 mm Hg. If the partial pressure of $O_2$ is found to be less than the threshold value, step 224 is executed in which the net effect of the blood $O_2$ level on the cardiac output is calculated using equations 4 and 6. If as a result of the comparison at step 222 $PaO_2$ is found to be greater than or equal to the threshold value, step 226 is executed in which the net effect of $O_2$ on the cardiac output is set to zero. At step 228 that follows, the net effects of the $CO_2$ and $O_2$ levels in the patient's arterial blood on the cardiac output are summed up using equation 7.

In the next step 229, the value of the patient's stroke volume is entered. This value is either monitored continuously or is measured prior to operation of the system at a desired posture and supplied to the processor as a constant. The stroke volume may be read from one of the input channels or stored in software if it is not continuously monitored. In step 230, cardiac output is calculated by multiplying the heart rate (in beats per second) by the stroke volume (in liters per beat). Using equation 1 at the next step 232, the sum of the effects of $CO_2$ and $O_2$ levels in the patient's arterial blood on the cardiac output, found at 228 ($Q'_c$), is subtracted from the cardiac output calculated at 230 (dQ/dT), to determine the net effect of the metabolic rate ratio on the blood flow, $Q'_M$.

Having found the value of $Q'_M$, the metabolic rate ratio is calculated using equations 8 and 9 at step 234. At step 236, the calculated value of the metabolic rate ratio, MRR, is compared with a minimum value of 1. If the metabolic rate ratio is less than this value, it is increased to 1 at step 238 and then step 240 is executed. However, if the calculated ratio is greater than or equal to the minimum value, step 240 is executed after step 236. At step 240 the values of 10 times MRR, and the heart rate in beats per minute, determined at either step 210 or 212, are transmitted to the output ports 70 and 72. After the execution of step 240, the program control returns to "A" and another loop is started.

CONCLUSION

There has been described a preferred embodiment of an apparatus and method for determining a patient's metabolic rate ratio. The present invention may be embodied in other specific forms without departing from the spirit or essential attributes thereof. Accordingly, reference should be made to the appended claims, rather than to the foregoing specification, as indicating the scope of the invention.

What is claimed is:

1. Apparatus comprising:
   (a) first means for providing data indicative of a cardiac function of a patient; and,
   (b) second means for determining the patient's metabolic rate ratio based upon the data provided by the first means.

2. Apparatus according to claim 1 further comprising third means for providing data indicative of oxygen and carbon dioxide concentrations of the patient, the second means determining the patient's metabolic rate ratio based upon the data provided by the first and third means.

3. Apparatus according to claim 2 wherein the third means comprises $CO_2$ and $O_2$ analyzers for analyzing exhaled gas of the patient.

4. Apparatus according to claim 2 wherein the third means comprises a $CO_2$ analyzer and a pulse oximeter.

5. Apparatus according to claim 2 wherein the second means comprises a processor programmed to determined the patient's metabolic rate ratio by:
   (a) determining, based upon the data indicative of the patient's oxygen and carbon dioxide concentrations, and data indicative of barometric pressure, the partial pressures of oxygen and carbon dioxide in arterial blood of the patient;
   (b) determining, based upon he results of step (a), net effects of oxygen and carbon dioxide in the arterial blood on cardiac output of the patient;
   (c) determining, based upon data indicative of cardiac output of the patient and the result of step (b), net effect of metabolic rate ratio on cardiac output of the patient; and,
   (d) determining, based upon the result of step (c), the metabolic rate ratio of the patient.

6. Apparatus according to claim 1 wherein the first means comprises a heart rate monitor.

7. Apparatus according to claim 6 wherein the heart rate monitor comprises a pulse monitor for providing a systolic pulse signal.

8. Apparatus according to claim 6 wherein the heart rate monitor comprises means for processing an ECG signal.

9. Apparatus according to claim 6 further comprising a stroke volume monitor.

10. Apparatus according to claim 1 wherein the first means comprises a cardiac output monitor.

11. Apparatus comprising:
    (a) first means for analyzing gas exhaled by a patient and providing output dates indicative of volume concentration of at least one of $CO_2$ and $O_2$ in the gas;
    (b) second means for providing data indicative of heart rate of the patient; and,
    (c) third means receiving data from the first and second means for computing therefrom data indicative of the patient's metabolic rate ratio.

12. Apparatus according to claim 11 wherein the first means further comprises $CO_2$, and $O_2$ analyzers.

13. Apparatus according to claim 11 wherein the first means comprises a $CO_2$ analyzer and a pulse oximeter.

14. Apparatus according to claim 11 further comprising fourth means for providing data indicative of the patient's stroke volume, the third means determining the patient's cardiac output from the heart rate and stroke volume data.

15. Apparatus according to claim 14 wherein the fourth means continuously monitors the patient's stroke volume and provides data indicative thereof.

16. Apparatus according to claim 14 wherein the data supplied by the fourth means is a constant value.

17. Apparatus according to claim 11 wherein the second means comprises:
    (a) a pulse detector; and,
    (b) means coupled to the pulse detector for counting pulses.

18. Apparatus according to claim 11 wherein the second means comprises an ECG unit.

19. Apparatus comprising:
    (a) a processor for determining a patient's metabolic rate ratio from data indicative of partial pressures of carbon dioxide and oxygen in the patient's arterial blood, the patient's heart rate and the patient's stroke volume;
    (b) a first analog to digital converter coupled to the processor;
    (c) a carbon dioxide analyzer coupled to the first analog to digital convertor for monitoring the amount of carbon dioxide exhaled by the patient;
    (d) a second analog to digital converter coupled to the processor;
    (e) an oxygen sensor coupled to the second analog to digital convertor for monitoring the amount of oxygen exhaled by the patient;
    (f) a third analog to digital convertor coupled to the processor;
    (g) means for supplying analog data indicative of stroke volume to the third analog to digital converter;
    (h) a counter circuit means coupled to the processor for counting the patient's systolic pulse; and,
    (i) a pulse detector coupled to the counter circuit means for monitoring the patient's systolic pulse signal.

20. Method of measuring a patient's metabolic rate ratio comprising the steps of:
    (a) providing data indicative of oxygen and carbon dioxide concentrations of the patient;
    (b) determining, based upon the data indicative of the patient's oxygen and carbon dioxide concentrations and data indicative of barometric pressure, the partial pressures of oxygen and carbon dioxide in arterial blood of the patient;
    (c) determining, based upon the results of step (b), net effects of oxygen and carbon dioxide in the arterial blood on cardiac output of the patient;
    (d) determining, based upon data indicative of cardiac output of the patient and the result of step (c), net effect of metabolic rate ratio on cardiac output of the patient; and,
    (e) determining, based upon the result of step (d), the metabolic rate ratio of the patient and providing output data indicative thereof.

21. Method according to claim 20 further comprising the step of:
    (a) providing data indicative of heart rate of the patient; and,
    (b) providing data indicative of stroke volume of the patient, data indicative of cardiac output of the patient being obtained by multiplying the data indicative of stroke volume by the data indicative of heart rate.

22. Method according to claim 21 further comprising the step of substituting the data indicative of heart rate with previously provided heart rate data when the data indicative of heart rate fails to fall within predetermined limits.

23. Method according to claim 20 wherein the data indicative of oxygen and carbon dioxide concentrations are provided by means of oxygen and carbon dioxide analyzers.

24. Method according to claim 23 wherein the partial pressures of oxygen and carbon dioxide in arterial blood of the patient are determined according to the following relationships:

$$PaCO_2 = C_{CO_2}(P_B - 47) - K_1$$

$$PaO_2 = C_{O_2}(P_B - 47) - K_2$$

Where:
(a) $PaO_2$ and $PaCO_2$ are the partial pressures of oxygen and carbon dioxide, respectively, in arterial blood of the patient in mmHg;
(b) $C_{O_2}$ and $C_{CO_2}$ are the volume concentrations of oxygen and carbon dioxide in exhaled gas of the patient, respectively;
(c) $K_1$ and $K_2$ are constants representing average differences between alveolar and arterial pressures of $CO_2$ and $O_2$, respectively, in mmHg;
(d) $P_B$ is the barometric pressure in mm Hg; and,
(e) 47 is the partial pressure of water vapor in alveoli space in mmHg.

25. Method according to claim 20 wherein the data indicative of oxygen concentration is provided by means of a pulse oximeter.

26. Method according to claim 25 wherein the partial pressure of oxygen in arterial blood of the patient is determined according to the following relationship:

$$PaO_2 = \frac{-\ln[1 - (SaO_2)^{\frac{1}{4}}]}{0.046}$$

where:
(a) $PaO_2$ is the partial pressure of oxygen in the arterial blood of the patient in mmHg; and,
(b) $SaO_2$ is arterial hemoglobin oxygen saturation provided by the oximeter.

27. Method according to claim 20 wherein, when the partial pressure of carbon dioxide in arterial blood fails to exceed a predetermined threshold, the net effect of carbon dioxide in arterial blood on cardiac output is set to a pre-established value, and when the partial pressure of carbon dioxide in arterial blood exceeds the predetermined threshold the net effect of carbon dioxide in arterial blood on cardiac output is determined according to the following relationship:

$$Q'(CO_2) = 0.0045(PaCO_2 - N)$$

where:
(a) $Q'(CO_2)$ is the net effect of arterial pressure of carbon dioxide on cardiac output in liters per second;
(b) $PaCO_2$ is the partial pressure of carbon dioxide in arterial blood of the patient in mmHg; and,
(c) N is the value of the predetermined threshold in mmHg.

28. Method according to claim 20 wherein, when the partial presure of oxygen in the arterial blood of the patient exceeds a predetermined threshold the net effect of oxygen in arterial blood of the patient on cardiac output is set to a pre-established value, and when the partial pressure of oxygen in the arterial blood of the patient fails to exceed the predetermined threshold the net effect of oxygen in arterial blood on cardiac output is determined according to the following relationship:

$$Q'(O_2) = 244.509 \times 10^{-4} T_0(X)$$
$$- 323.328 \times 10^{-4} T_1(X) + 105.044 \times 10^{-4} T_2(X) -$$
$$143.505 \times 10^{-5} T_3(X)$$

where:
(a) $Q'(O_2)$ is the net effect of arterial pressure of oxygen on cardiac output in liters per second;
(b) $T_j(X)$ is the Chebyshev polynomial of the first kind of degree (j) and argument (X);
(c)

$$X = \frac{2PaO_2 - 115}{65};$$

and,
$PaO_2$ arterial pressure of oxygen in mm Hg.

29. Method according to claim 2 wherein the net effects of oxygen and carbon dioxide in the arterial blood on cardiac output is determined according to the following relationship:

$$Q'_C 32 \ Q'(CO_2) + Q'(O_2)$$

where:
(a) $Q'_C$ is the net effects of oxygen and carbon dioxide in arterial blood on the cardiac output;
(b) $Q'(CO_2)$ is the net effect of arterial pressure of carbon dioxide on the cardiac output; and,
(c) $Q'(O_2)$ is the net effect of arterial pressure of oxygen on the cardiac output.

30. Method according to claim 20 wherein the net effect of the metabolic rate ratio on the cardiac output of the patient is determined according to the following relationship:

$$\frac{dQ}{dT} = Q'_M + Q'_C$$

where:
(a)

$$Y = \frac{2MRR - 7}{5}$$

is the cardiac output or blood flow;
(b) $Q'_M$ is the net effect of the metabolic rate ratio on the cardiac output; and,
(c) $Q'_C$ is the net effects of oxygen and carbon dioxide in arterial blood on the cardiac output.

31. Method according to claim 20 wherein the metabolic rate ratio is calculated according to the following relationships:

$$Q'_M = 158.5674 \times 10^{-3} T_0(Y) + 617.519 \times 10^{-4} T_1(Y)$$

and $$\frac{dQ}{dT}$$

where:
(a) $Q'_M$ is the net effect of the metabolic rate ratio on cardiac output in liters per second;
(b) $T_j(Y)$ is the Chebyshev polynomial of the first kind and degree (j) with argument (Y); and,
(c) MRR is the metabolic rate ratio.

* * * * *

UNITED STATES PATENT AND TRADEMARK OFFICE
CERTIFICATE OF CORRECTION

PATENT NO. : 4,909,259
DATED : March 20, 1990
INVENTOR(S) : Fleur Taher Tehrani

It is certified that error appears in the above-identified patent and that said Letters Patent is hereby corrected as shown below:

Col. 7, line 43, "100K" should be --100--;

Col. 7, line 55, "Carciac" should be --Cardiac--;

Col. 8, line 1, "$p^{ACO}{}_2$" should be --$PaCO_2$--;

Col. 8, line 33, "$O_{20}$" should be --$O_2$--;

Col. 9, line 3, "$Q'_m$" should be --$Q'_M$--;

Col. 11, lines 22-23, "determined" should be --determine--;

Col. 11, line 52, "dates" should be --data--;

Col. 14, line 19, "2" should be --20--;

Col. 14, line 24, "$Q'c^{32}$" should be --$Q'_C =$ --;

Col. 14, lines 42-47, "(a) $\underline{Y = 2MRR - 7}$ is the cardiac output or
                                    5
blood flow" should be  --(a) $\underline{dQ}$ is the cardiac output or blood flow"--;
                              $dT$

UNITED STATES PATENT AND TRADEMARK OFFICE
CERTIFICATE OF CORRECTION

PATENT NO. : 4,909,259

DATED : March 20, 1990

INVENTOR(S) : Fleur Taher Tehrani

It is certified that error appears in the above-identified patent and that said Letters Patent is hereby corrected as shown below:

Col. 14, line 60, "$\frac{dQ}{dT}$" should be -- $Y = \frac{2MRR - 7}{5}$ --.

Signed and Sealed this

Thirtieth Day of April, 1991

*Attest:*

HARRY F. MANBECK, JR.

*Attesting Officer*     *Commissioner of Patents and Trademarks*